United States Patent [19]

Junino et al.

[11] Patent Number: 4,692,166

[45] Date of Patent: Sep. 8, 1987

[54] USE OF HALOGENATED 4,5-METHYLENEDIOXYPHENOL IN THE DYEING OF KERATINOUS FIBRES

[75] Inventors: Alex Junino, Livry-Gargan; Gerard Lang, Saint-Gratien; Herve Andrean, Paris; Jean Cotteret, Limay, all of France

[73] Assignee: L'Oreal, Paris, France

[21] Appl. No.: 841,813

[22] Filed: Mar. 20, 1986

[30] Foreign Application Priority Data

Mar. 21, 1985 [FR] France ................................ 85 04224

[51] Int. Cl.⁴ ..................... A61K 7/13; C07D 317/48; C07D 317/52; C07D 317/54
[52] U.S. Cl. .......................................... 8/410; 8/406; 8/408; 549/434
[58] Field of Search .......................... 8/408, 406, 410; 549/434

[56] References Cited

U.S. PATENT DOCUMENTS 4,395,262 7/1983 Konrad et al. .......................... 8/410
4,514,490 4/1985 Seto et al. ............................ 430/505

FOREIGN PATENT DOCUMENTS 004366 3/1979 European Pat. Off. .
2111490 7/1983 United Kingdom .

OTHER PUBLICATIONS

Alexander et al., *Journal of Organic Chemistry*, vol. 23, Mack Printing, PA., 1958, pp. 1969-1970.
Monbalin et al., Research Disclosure #20219, 1981.

*Primary Examiner*—Paul Lieberman
*Assistant Examiner*—Linda Skaling
*Attorney, Agent, or Firm*—Cushman, Darby & Cushman

[57] ABSTRACT

Use for dyeing keratinous fibres, and especially human hair, on a compound corresponding to the formula:

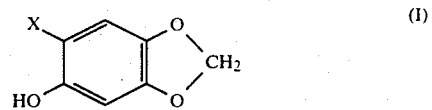

in which X denotes a bromine or chlorine atom.

18 Claims, No Drawings

USE OF HALOGENATED 4,5-METHYLENEDIOXYPHENOL IN THE DYEING OF KERATINOUS FIBRES

The present invention relates to the use in the dyeing of keratinous fibres, especially human hair, of halogenated 4,5-methylenedioxyphenol, to the dyeing compositions containing this compound and also to a dyeing process employing it.

The coloring of keratinous fibres, such as human hair, known as "permanent coloring" is obtained by means of the use of so-called "oxidation" dyes which, after development of their dyeing power in an oxidizing medium, enable a coloring to be obtained which is resistant to several applications of shampoo, to light and to adverse weather conditions. Oxidation dyes are generally not dyes in themselves, but are intermediate compounds initially having little or no color, commonly known as "oxidation bases or oxidation dye precursors", which develop their dyeing power in an oxidizing medium generally consisting of hydrogen peroxide to give rise, in a basic medium, to a dye according to a process of oxidative condensation, either of the oxidation dye precursor with itself, or of the base or oxidation dye precursor of the para or ortho type with a compound known as a "modifier or coupler".

The variety of molecules involved, consisting of the oxidation dye precursors of the para or ortho type and the couplers, enables a rich palette of colors to be obtained as regards natural, black, ashen or blonde shades, and shades possessing glints.

The coloring obtained by means of these oxidation dyes must, however, satisfy a number of requirements:

It must be devoid of disadvantages from the toxicological standpoint, enable shades to be obtained within the desired intensity and possess good stability to external agents (light, adverse weather conditions, washing, permanent waving, acidic or basic perspiration, friction);

the dyes must also enable white hair to be covered and be as little selective as possible, that is to say show the smallest possible range of coloring over the entire length of the hair fibre, which may be differentially sensitized between the ends and the roots.

Furthermore, means are sought whereby the redness of certain colorings obtained by coupling between the para type dye precursors and couplers may be "diminished".

The applicants have discovered that the use of halogenated 4,5-methylenedioxyphenol as a coupler in oxidation dyeing compositions enabled shades to be obtained, with the para oxidation dye precursors customarily used in oxidation dyeing, which fell within the green tones, enabling, inter alia, the redness of some colorings to be diminished to lead to natural tints on keratinous fibres, and on human hair in particular.

This is especially important for compositions containing para type dye precursors, such as p-phenylenediamines or p-aminophenols, combined with couplers of the m-aminophenol or m-phenylenediamine type. The additional coupling of these dye precursors with the halogenated 4,5-methylenedioxyphenols according to the invention enables, in particular, less reddish and more natural tints to be obtained, as a result of the provision of green.

The subject of the present invention is consequently the use in dyeing compositions for the permanent coloring, or oxidation dyeing, of keratinous fibres, especially human hair, of halogenated 4,5-methylenedioxyphenol as a coupler with the oxidation dye precursors capable of coupling therewith.

The subject of the invention is also the dyeing compositions containing a halogenated 4,5-methylenedioxyphenol as a coupler, and also the process of dyeing keratinous fibres, and especially human hair, employing such a coupler.

Other subjects of the invention will emerge on reading the description and examples which follow.

The compounds which are used according to the invention as couplers in permanent or oxidation dyeing of keratinous fibres, and especially human hair, correspond to the formula:

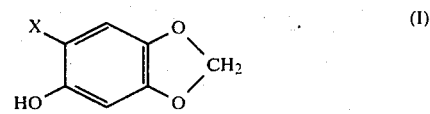

(I)

in which X denotes a chlorine or bromine atom.

The coupler of formula (I) is used with oxidation dye precursors capable of forming a dye by coupling therewith.

The oxidation dyeing compositions for keratinous fibres, and especially human hair, according to the invention and employing the compound of formula (I) are essentially characterized in that they contain, in a cosmetically acceptable medium and in sufficient amounts for dyeing the said fibres:

(a) at least one para type oxidation dye precursor which contains either two functional amino groups or an amino group and a hydroxy group bound in the para position on the benzene ring, or alternatively on heterocyclic rings such as pyridine rings, these precursors being present in the form of free base or in the form of addition salts with an acid; and (b) at least one coupler corresponding to the formula (I):

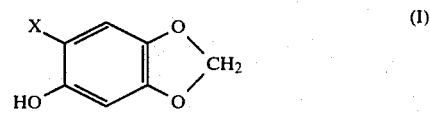

(I)

in which X denotes a chlorine or bromine atom.

The oxidation dye precursors which are especially preferred and which can be used according to the invention are chosen from the p-phenylenediamines corresponding to the general formula (II):

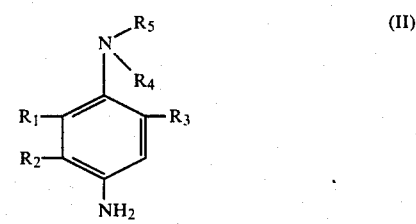

(II)

or the corresponding salts, in which $R_1$, $R_2$ and $R_3$ are identical or different and denote a hydrogen atom, an alkyl radical having 1 to 4 carbon atoms or an alkoxy radical having 1 to 4 carbon atoms, and $R_4$ and $R_5$ are identical or different and denote a hydrogen atom or an alkyl, hydroxyalkyl, alkoxyalkyl, carbamylalkyl, mesylaminoalkyl, acetylaminoalkyl, ureidoalkyl, carbethoxyaminoalkyl, piperidinoalkyl or morpholinoalkyl radical, the alkyl or alkoxy groups denoted by $R_4$ and $R_5$ having from 1 to 4 carbon atoms, or alternatively $R_4$ and $R_5$ can form, together with the nitrogen atom to which they are linked, a piperidino or morpholino heterocyclic system, with the proviso that $R_1$ or $R_3$ denotes a hydrogen atom when $R_4$ and $R_5$ do not denote a hydrogen atom.

Among the compounds of formula (II), there may be mentioned p-phenylenediamine, p-tolylenediamine, methoxy-para-phenylenediamine, chloro-para-phenylenediamine, 2,6-dimethyl-p-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N-diethylaniline, N,N-bis($\beta$-hydroxyethyl)-para-phenylenediamine, 3-methyl-4-amino-N,N-bis($\beta$-hydroxyethyl)aniline, 3-chloro-4-amino-N,N-bis($\beta$-hydroxyethyl)aniline, 4-amino-N-ethyl-N-(carbamylmethyl)aniline, 3-methyl-4-amino-N-ethyl-N-(carbamylmethyl)aniline, 4-amino-N-ethyl-N-($\beta$-piperidinoethyl)aniline, 3-methyl-4-amino-N-ethyl-N-($\beta$-piperidinoethyl)aniline, 4-amino-N-ethyl-N-($\beta$-morpholinoethyl)aniline, 3-methyl-4-amino-N-ethyl-N-($\beta$-morpholinoethyl)aniline, 4-amino-N-ethyl-N-($\beta$-acetylaminoethyl)aniline, 4-amino-N-($\beta$-methoxyethyl)aniline, 3-methyl-4-amino-N-ethyl-N-($\beta$-acetylaminoethyl)aniline, 4-amino-N-ethyl-N-($\beta$-mesylaminoethyl)aniline, 3-methyl-4-amino-N-ethyl-N-($\beta$-mesylaminoethyl)aniline, 4-amino-N-ethyl-N-($\beta$-sulphoethyl)aniline, 3-methyl-4-amino-N-ethyl-N-($\beta$-sulphoethyl)aniline, N-(4'-aminophenyl)morpholine and N-(4'-aminophenyl)piperidine. These para type oxidation dye precursors can be introduced into the dyeing composition in the form of free base or in salt form, such as in the form of hydrochloride, hydrobromide or sulphate.

Couplers of formula (I) can also be used with p-aminophenols to give shades which are especially stable to light, adverse weather conditions and washing, after development in the presence of an oxidizing agent. Among p-aminophenols, there may be mentioned p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol and 2,5-dimethyl-4-aminophenol.

The couplers of formula (I) can also be used with heterocyclic para oxidation dye precursors, among which 2,5-diaminopyridine and 2-hydroxy-5-aminopyridine may be mentioned.

These compositions can also contain ortho type oxidation dye precursors, such as ortho-aminophenols, ortho-phenylenediamines, and orthodiphenols such as 1-amino-2-hydroxybenzene, 6-methyl-1-hydroxy-2-aminobenzene and 4-methyl-1-amino-2-hydroxybenzene.

The dyeing compositions according to the invention containing the coupler of formula (I) can optionally contain other couplers known per se such as meta-diphenols, meta-aminophenols, meta-phenylenediamines, meta-acylaminophenols, meta-ureidophenols, meta-carbalkoxyaminophenols, $\alpha$-naphthol and couplers possessing an active methylene group such as $\beta$-keto compounds and pyrazolones.

There may be mentioned in particular, by way of example, (2,4-dihydroxyphenoxy)ethanol, 2,4-dihydroxyanisole, meta-aminophenol, resorcinol monomethyl ether, 2-methyl-5-aminophenol, 2-methyl-5-($\beta$-hydroxyethyl)aminophenol, 2-methyl-5-($\beta$-mesylaminoethyl)aminophenol, 2,6-dimethyl-3-aminophenol, 6-hydroxybenzomorpholine, 2,4-diaminoanisole, (2,4-diaminophenoxy)ethanol, 6-aminobenzomorpholine, [2-($\beta$-hydroxyethyl)amino-4-aminophenoxy]ethanol, 2-amino-4-($\beta$-hydroxyethyl)aminoanisole, 2,4-diaminophenyl $\beta,\gamma$-dihydroxypropyl ether and (2,4-diaminophenoxy)ethylamine, and the salts thereof.

As is wellknown, for the purpose of imparting shades to the colorings provided by oxidation dye precursors, or enriching these colorings with glints, direct dyes, such as azo or anthraquinone dyes or nitro derivatives of the benzene series, can be added to these compositions.

The combination of the para compounds and the couplers used in the dyeing compositions according to the invention preferably represent from 0.3 to 7% by weight of the said composition. The concentration of compounds (I) can vary between 0.05 and 3.5% of the weight of the total composition.

The cosmetically acceptable medium is generally aqueous and its pH can vary between 8 and 11, and is preferably between 9 and 11.

It is adjusted to the desired value using an alkalinizing agent such as ammonia solution, alkali metal carbonates or alkanolamines such as mono-, di- or tri-ethanolamine.

The dyeing compositions according to the invention also contain, in their preferred form of production, anionic, cationic, nonionic or amphoteric surfactants, or mixtures thereof. Among these surfactants, there may be mentioned more especially alkylbenzenesulphonates, alkylnaphthalenesulphonates, sulphates, fatty alcohol ether sulphates and sulphonates, quaternary ammonium salts such as trimethylcetylammonium bromide and cetylpyridinium bromide, fatty acid ethanolamides which may optionally be oxyethylenated; polyoxyethylenated acids, polyoxyethylenated alcohols and polyoxyethylenated amines, polyglycerolated alcohols, polyoxyethylenated or polyglycerolated alkylphenols and also polyoxyethylenated alkyl sulphates. The surfactants are present in the compositions according to the invention in proportions of between 0.5 and 40% by weight, and preferably between 4 and 30% be weight, relative to the total weight of the composition.

These compositions can also contain organic solvents to solubilize compounds which would be insufficiently soluble in water. Among these solvents, there may be mentioned, by way of example, $C_1$-$C_4$ lower alcohols such as ethanol and isopropanol, glycerol, glycols or glycol ethers such as 2-butoxyethanol, ethylene glycol, propylene glycol, and diethylene glycol monoethyl ether and monomethyl ether, and also similar products and the mixtures thereof. The solvents are preferably present in a proportion of between 1 and 40% by weight, and especially between 5 and 30% by weight, relative to the total weight of the composition.

The thickening agents which can be added to the compositions according to the invention are chosen, in particular, from the group consisting of sodium alginate, gum arabic, cellulose derivatives such as methylcellulose, hydroxyethylcellulose, hydroxypropylcellulose, hydroxymethylcellulose and carboxymethylcellulose, acrylic acid polymers and xanthan gum. Inorganic thickening agents such as bentonite can also be used. These thickening agents are preferably present in proportions of between 0.1 and 5% by weight, and especially between 0.5 and 3% by weight, relative to the total weight of the composition.

The compositions can contain antioxidants chosen, in particular, from sodium sulphite, thioglycollic acid, sodium bisulphite, ascorbic acid and hydroquinone. These antioxidants are present in the composition in proportions of between 0.05 and 1.5% by weight relative to the total weight of the composition.

Other adjuvants which can be used according to the invention are, for example, penetrants, sequestering agents, buffers and perfumes.

The dyeing compositions according to the invention can take various forms, such as liquid, cream or gel form, or any other form suitable for carrying out dyeing of keratinous fibres and especially human hair. They can also be packaged in aerosol cans in the presence of a propellant.

The dyeing compositions according to the invention, containing an oxidation dye precursor and a coupler of formula (I), are used in processes for dyeing keratinous fibres, and especially human hair, according to a process which employs development with an oxidizing agent.

According to this process, the dyeing composition described above is mixed at the time of use with a sufficient amount of an oxidizing solution, and the mixture obtained is then applied on the hair.

The oxidizing solution contains oxidizing agents such as hydrogen peroxide, urea peroxide or persalts such as ammonium persulphate. The solution of "20 volumes" (6% be weight) hydrogen peroxide is preferably used.

The mixture obtained is applied on the hair and left in place for 10 to 40 minutes, preferably 15 to 30 minutes, after which the hair is rinsed, washed with shampoo, rinsed again and dried.

Another process employing the coupler of formula (I) according to the invention consists in dyeing the hair according to a multi-stage process which consists, in one of the stages, in applying the para oxidation dye precursor by means of a composition defined above and, in another stage, applying the coupler of formula (I); the oxidizing agent being present in the composition applied in the second stage or alternatively added onto the keratinous fibres themselves in a third stage and the exposure and drying or washing conditions being identical.

The compounds are prepared according to a process of halogenation of 4,5-methylenedioxyphenol, by the action of bromine on 4,5-methylenedioxyphenol in acetic acid in one case, and the action of sulphuryl chloride in ethyl ether in the other case.

The examples which follow are intended to illustrate the invention without thereby being limitative in nature.

PREPARATION EXAMPLE 1

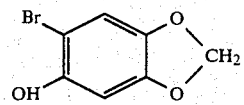

2-Bromo-4,5-methylenedioxyphenol

To a solution of 0.18 mol (25 g) of 4,5-methylenedioxyphenol in 125 ml of glacial acetic acid, a solution of 0.16 mol (29 g) of bromine in 145 ml of glacial acetic acid is added slowly, the temperature of the reaction medium being maintained at between 15° and 25° C. When the addition is complete, the reaction medium is poured into 1.5 liters of ice-cold water. The expected product precipitates. After being drained, it is washed with water until the solvent has been removed. After being dried under vacuum in the presence of potassium hydroxide, it is recrystallized from a petroleum ether/ethyl acetate mixture or from cyclohexane. It melts at 84° C. (decomposition).

Analysis of the product obtained gives the following results:

| Analysis | Calculated for $C_7H_5O_3Br$ | Found |
| --- | --- | --- |
| C | 38.73 | 38.84 |
| H | 2.30 | 2.35 |
| O | 22.13 | 21.90 |
| Br | 36.84 | 36.75 |

PREPARATION EXAMPLE 2

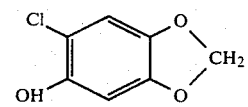

2-Chloro-4,5-methylenedioxyphenol

To a solution of 0.18 mol (25 g) of 4,5-methylenedioxyphenol in 125 ml of ethyl ether, 17 ml of sulphuryl chloride are added at a temperature below 35° C. As soon as the addition is complete, the ethyl ether is evaporated off at room temperature. The dry residue thereby obtained is taken up with 2N sodium hydroxide. The mixture is filtered to remove a resin. The filtrate is acidified with 2N hydrochloric acid; the expected product precipitates. After being washed with water and dried under vacuum in the presence of phosphorus pentoxide, it is recrystallized from a cyclohexane/benzene mixture. It melts at 95° C.

Analysis of the product obtained gives the following results:

| Analysis | Calculated for $C_7H_5O_3Cl$ | Found |
| --- | --- | --- |
| C | 48.69 | 48.77 |
| H | 2.89 | 2.91 |
| O | 27.82 | 27.93 |
| Cl | 20.58 | 20.63 |

EXAMPLE 1

The following composition is prepared:

| | |
| --- | --- |
| p-Phenylenediamine | 0.27 g |
| 2-Bromo-4,5-methylenedioxyphenol | 0.542 g |
| Polyglycerolated oleyl alcohol containing 2 moles of glycerol | 4.5 g |
| Polyglycerolated oleyl alcohol containing 4 moles of glycerol | 4.5 g |
| ETHOMEEN O 12, from ARMOON HESS CHEMICAL Ltd. (oxyethylenated oleylamine containing 12 moles of ethylene oxide) | 4.5 g |
| COMPERLAN KD, from HENKEL (coconut diethanolamides) | 9 g |
| Propylene glycol | 4 g |

-continued

| | |
|---|---|
| 2-Butoxyethanol | 8 g |
| Ethanol, 96° | 6 g |
| MASQUOL DTPA, from PROTEX (diethylenetriaminepentaacetic acid pentasodium salt) | 2 g |
| Hydroquinone | 0.15 g |
| Sodium bisulphite solution, 35° Be | 1.3 g |
| Ammonia solution, 22° Be | 10 g |
| Water qs | 100 g |

The pH equals 10.3.

At the time of use, 100 g of "20 volumes" (6% by weight) hydrogen peroxide are added.

When applied for 20 minutes at 30° C. on naturally grey hair, the mixture endows it, after shampooing and rinsing, with a sustained bronze coloring.

EXAMPLE 2

The following composition is prepared:

| | |
|---|---|
| p-Phenylenediamine | 0.27 g |
| 2-Chloro-4,5-methylenedioxyphenol | 0.542 g |
| Polyglycerolated oleyl alcohol containing 2 moles of glycerol | 4.5 g |
| Polyglycerolated oleyl alcohol containing 4 moles of glycerol | 4.5 g |
| ETHOMEEN O 12, from ARMOON HESS CHEMICAL Ltd. (oxyethylenated oleylamine containing 12 moles of ethylene oxide) | 4.5 g |
| COMPERLAN KD, from HENKEL (coconut diethanolamides) | 9 g |
| Propylene glycol | 4 g |
| 2-Butoxyethanol | 8 g |
| Ethanol, 96° | 6 g |
| MASQUOL DTPA, from PROTEX (diethylenetriaminepentaacetic acid pentasodium salt) | 2 g |
| Hydroquinone | 0.15 g |
| Sodium bisulphite solution, 35° Be | 1.3 g |
| Ammonia solution, 22° Be | 10 g |
| Water qs | 100 g |

The pH equals 10.3.

At the time of use, 100 g of "20 volumes" hydrogen peroxide are added.

When applied for 20 minutes at 30° C. on bleached hair, the mixture endows it, after shampooing and rinsing, with a bronze coloring.

EXAMPLE 3

The following composition is prepared:

| | |
|---|---|
| 4-(β-Methoxyethylamino)aniline dihydrochloride | 0.598 g |
| 2-Bromo-4,5-methylenedioxyphenol | 0.542 g |
| Polyglycerolated oleyl alcohol containing 2 moles of glycerol | 4.5 g |
| Polyglycerolated oleyl alcohol containing 4 moles of glycerol | 4.5 g |
| ETHOMEEN O 12, from ARMOON HESS CHEMICAL Ltd. (oxyethylenated oleylamine containing 12 moles of EO (ethylene oxide) | 4.5 g |
| COMPERLAN KD, from HENKEL (coconut diethanolamides) | 9 g |
| Propylene glycol | 4 g |
| 2-Butoxyethanol | 8 g |
| Ethanol, 96° | 6 g |
| MASQUOL DTPA, from PROTEX (diethylenetriaminepentaacetic acid pentasodium salt) | 2 g |
| Hydroquinone | 0.15 g |
| Sodium bisulphite solution, 35° Be | 1.3 g |
| Ammonia solution, 22° Be | 10 g |
| Water qs | 100 g |

The pH equals 10.3.

At the time of use, 100 g of "20 volumes" hydrogen peroxide are added.

When applied for 20 minutes at 30° C. on permanent-waved grey hair, the mixture endows it, after shampooing and rinsing, with a chestnut coloring.

EXAMPLE 4

The following composition is prepared:

| | |
|---|---|
| 4-(β-Methoxyethylamino)aniline dihydrochloride | 0.598 g |
| 2-Chloro-4,5-methylenedioxyphenol | 0.431 g |
| Polyglycerolated oleyl alcohol containing 2 moles of glycerol | 4.5 g |
| Polyglycerolated oleyl alcohol containing 4 moles of glycerol | 4.5 g |
| ETHOMEEN O 12, from ARMOON HESS CHEMICAL Ltd. (oxyethylenated oleylamine containing 12 moles of ethylene oxide) | 4.5 g |
| COMPERLAN KD, from HENKEL (coconut diethanolamides) | 9 g |
| Propylene glycol | 4 g |
| 2-Butoxyethanol | 8 g |
| Ethanol, 96° | 6 g |
| MASQUOL DTPA, from PROTEX (diethylenetriaminepentaacetic acid pentasodium salt) | 2 g |
| Hydroquinone | 0.15 g |
| Sodium bisulphite solution, 35° Be | 1.3 g |
| Ammonia solution, 22° Be | 10 g |
| Water qs | 100 g |

The pH equals 10.3.

At the time of use, 100 g of "20 volumes" hydrogen peroxide are added.

When applied for 20 minutes at 30° C. on bleached hair, the mixture endows it, after shampooing and rinsing, with a dark ash blonde coloring.

EXAMPLE 5

The following dyeing composition is prepared:

| | |
|---|---|
| N,N—bis(β-hydroxyethyl)-p-phenylenediamine dihyrochloride | 0.15 g |
| p-Aminophenol | 0.267 g |
| m-Aminophenol | 0.011 g |
| 2-Methyl-5-(β-hydroxyethyl)aminophenol | 0.09 g |
| 2-Chloro-4,5-methylenedioxyphenol | 0.093 g |
| (2,4-Diaminophenoxy)ethanol dihydrochloride | 0.04 g |
| Hydroquinone | 0.15 g |
| Carbopol 934, sold by GOODRICH CHEMICALS (crosslinked polyacrylic acid) | 2 g |
| Ammonia, 22° Be | 10 g |
| Water, qs | 100 g |
| pH 10 | |

At the time of use, 100 g of "20 volumes" hydrogen peroxide are added.

When applied for 20 minutes at 30° C. on hair which is naturally 90% white, this mixture endows it, after shampooing and rinsing, with a dark ash blonde coloring.

EXAMPLE 6

The following dyeing composition is prepared:

| | |
|---|---|
| p-Phenylenediamine | 0.16 g |
| meta-Aminophenol | 0.13 g |
| p-Aminophenol | 0.15 g |
| o-Aminophenol | 0.126 g |
| 2,4-Dihydroxyanisol | 0.11 g |
| 2-Bromo-4,5-methylenedioxyphenol | 0.10 g |
| 2-Amino-4-(β-hydroxyethyl)aminoanisol dihydrochloride | 0.055 g |
| Alfol C 16/18, sold by CONDEA (cetyl/stearyl alcohol) | 8 g |
| Lanette wax E, sold by HENKEL (sodium salt of sulphated cetyl/stearyl alcohol) | 0.5 g |
| Cemulsol B, sold by RHONE POULENC (ethoxylated castor oil) | 1 g |
| Oleic diethanolamide | 1.5 g |
| Masquol DTPA, sold by PROTEX (diethylene-triaminepentaacetic acid pentasodium salt) | 2.5 g |
| Mercaptosuccinic acid | 0.3 g |
| Ammonia, 22° Be | 11 g |
| Water qs | 100 g |
| pH 10.5 | |

At the time of use, 100 g of "20 volumes" hydrogen peroxide are added. When applied for 25 minutes at 30° C. on hair which is naturally 90% white, this mixture endows it, after shampooing and rinsing, with an ashen pale chestnut coloring.

EXAMPLE 7

The following dyeing mixture is prepared:

| | |
|---|---|
| p-Phenylenediamine | 0.1 g |
| p-Aminophenol | 0.13 g |
| m-Aminophenol | 0.05 g |
| 2-Methyl-5-(β-hydroxyethyl)aminophenol | 0.14 g |
| 2-Chloro-4,5-methylenedioxyphenol | 0.15 g |
| CELLOSIZE WP 03, sold by UNION CARBIDE (hydroxyethylcellulose) | 2 g |
| Ammonium lauryl sulphate | 5 g |
| 2-Butoxyethanol | 15 g |
| Ethanol, 96° | 5 g |
| Masquol DTPA, sold by PROTEX (diethylene-triaminepentaacetic acid pentasodium salt) | 2 g |
| Ammonium thiolactate | 0.8 g |
| Ammonia, 22° Be | 10 g |
| Water qs | 100 g |
| pH 10 | |

At the time of use, 100 g of "20 volumes" hydrogen peroxide are added. When applied for 25 minutes at 30° C. on bleached hair, the mixture endows it, after shampooing and rinsing, with a golden pale chestnut coloring.

We claim:

1. Oxidation dyeing composition for human hair, comprising
in a cosmetically acceptable medium, and in sufficient amounts for dyeing the said human hair:
(a) one or several para type oxidation dye precursor containing two amino groups or an amino group and a hydroxy group bound in the para position on benzene rings, or alternatively on heterocyclic rings, this precursor being present in the form of free base or in salt form;
(b) at least one coupler of formula (I):

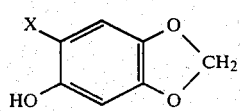

in which X denotes a chlorine or bromine atom.

2. Composition according to claim 1, wherein
the para type oxidation dye precursor is chosen from the p-phenylenediamines of general formula (II):

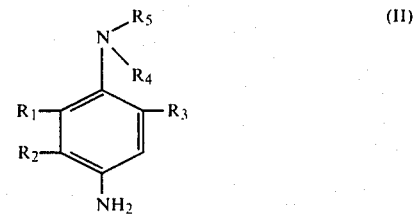

or the corresponding salts, in which $R_1$, $R_2$ and $R_3$ are identical or different and denote a hydrogen atom, an alkyl radical having 1 to 4 carbon atoms or an alkoxy radical having 1 to 4 carbon atoms, and $R_4$ and $R_5$ are identical or different and denote a hydrogen atom or an alkyl, hydroxyalkyl, alkoxyalkyl, carbamylalkyl, mesylaminoalkyl, acetylaminoalkyl, ureidoalkyl, carbethoxyaminoalkyl, piperidinoalkyl or morpholinoalkyl radical, the alkyl and alkoxy groups in $R_4$ and $R_5$ having from 1 to 4 carbon atoms, or alternatively $R_4$ and $R_5$ form, together with the nitrogen atom to which they are linked, a piperidino or morpholino heterocyclic system, with the proviso that $R_1$ or $R_3$ denotes a hydrogen atom when $R_4$ and $R_5$ do not denote a hydrogen atom.

3. Composition according to claim 1, wherein
the para-phenylenediamines are selected from the group consisting of: para-phenylenediamine, para-tolylenediamine, methoxy-para-phenylenediamine, chloro-para-phenylenediamine, 2,6-dimethyl-para-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, 3-methyl-4-amino-N,N-diethylaniline, N,N-bis(β-hydroxyethyl)-para-phenylenediamine, 3-methyl-4-amino-N,N-bis(β-hydroxyethyl)aniline, 3-chloro-4-amino-N,N-bis(β-hydroxyethyl)aniline, 4-amino-N-ethyl-N-(carbamylmethyl)aniline, 3-methyl-4-amino-N-ethyl-N-(carbamylmethyl)aniline, 4-amino-N-ethyl-N-(β-piperidinoethyl)aniline, 3-methyl-4-amino-N-ethyl-N-(β-piperidinoethyl)aniline, 4-amino-N-ethyl-N-(β-morpholinoethyl)aniline, 3-methyl-4-amino-N-ethyl-N-(β-morpholinoethyl)aniline, 4-amino-N-ethyl-N-(β-acetylaminoethyl)aniline, 4-amino-N-(β-methoxyethyl)aniline, 3-methyl-4-amino-N-ethyl-N-(β-acetylaminoethyl)aniline, 4-amino-N-ethyl-N-(β-mesylaminoethyl)aniline, 3-methyl-4-amino-N-ethyl-N-(β-mesylaminoethyl)aniline, 4-amino-N-ethyl-N-(β-sulphoethyl)aniline, 3-methyl-4-amino-N-ethyl-N-(β-sulphoethyl)aniline, N-(4'-aminophenyl)morpholine and N-(4'-aminophenyl)piperidine.

4. Composition according to claim 1 wherein as para type oxidation dye precursors, a para-aminophenol is used which is selected from the group consisting of para-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol and 2,5-dimethyl-4-aminophenol.

5. Composition according to claim 1, wherein the para type dye precursor is selected from the group consisting of 2,5-diaminopyridine and 2-hydroxy-5-aminopyridine.

6. Composition according to claim 1 which further contains ortho type oxidation dye precursor selected from the group consisting of ortho-phenylene-diamines, ortho-aminophenols and ortho-diphenols.

7. Composition according to claim 1 which further contains couplers different from those of formula (I), selected from the group consisting of meta-diphenols, meta-aminophenols, meta-phenylenediamines, meta-acylaminophenols, meta-ureidophenols, meta-carbalkoxyaminophenols, α-naphthol, β-keto couplers containing an active methylene group, and pyrazolones.

8. Composition according to claim 1 which further contains couplers other than those of formula (I), selected from the group consisting of (2,4-dihydroxyphenoxy)ethanol, 2,4-dihydroxyanisole, meta-aminophenol, resorcinol monomethyl ether, 2-methyl-5-aminophenol, 2-methyl-5-(β-hydroxyethyl)aminophenol, 2-methyl-5-(β-mesylaminoethyl)aminophenol, 2,6-dimethyl-3-aminophenole, 6-hydroxybenzomorpholine, 2,4-diaminoanisol, (2,4-diaminophenoxy)ethanol, 2-amino-4-(β-hydroxyethyl)aminoanisole, 2,4-diaminophenyl β,γ-dihydroxypropyl ether, (2,4-diaminophenoxy)ethylamine, 6-aminobenzomorpholine and [2-(β-hydroxyethyl)amino-4-aminophenoxy]ethanol, and the salts thereof.

9. Composition according to claim 1, wherein the para type dye precursors and the couplers are present in proportions of between 0.3 and 7% by weight.

10. Composition according to claim 1 wherein the coupler of formula (I) is present in proportions of between 0.05 an 3.5% by weight relative to the total weight of the composition.

11. Composition according to claim 1 having a pH between 8 and 11.

12. Composition according to claim 1 which further contains anionic, cationic, nonionic or amphoteric surfactants, or mixtures thereof, in proportions of 0.5 to 40% by weight.

13. Composition according to claim 1 which further contains, in addition to water, solvents chosen from C$_1$–C$_4$ lower alkanols, glycerol, glycols or glycol ethers, present in proportions of between 1 and 40% by weight.

14. Composition according to claim 1 which further contains thickening agents selected from the group consisting of sodium alginate, gum arabic, cellulose derivatives, acrylic acid polymers, xanthan gum and inorganic thickeners, in proportions of 0.1 to 5% by weight.

15. Composition according to claim 1 which further contains antioxidants in proportions of 0.05 to 1.5% by weight.

16. A method for dyeing human hair comprising applying to said hair a hair dyeing amount of an oxidation hair dye composition comprising in a cosmetically acceptable medium an oxidation dye precursor and a coupler of the formula

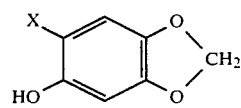

wherein X represents bormine or chlorine.

17. A method for dyeing human hair performed in several stages which comprises applying, in one of the stages, on said human hair coloring amounts of a para-type oxidation dye precursor, and in another stage a coloring amount of a coupler of the formula

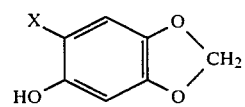

wherein X represents bromine or chlorine, an oxidizing agent being applied in a second stage or alternatively being applied onto said human hair in a third stage.

18. Method for permanent dyeing of keratinous fibres and especially human hair, which comprises applying on said fibers coloring amounts of a dyeing composition said dyeing composition being mixed at the time of use with a sufficient amount of an oxidizing solution.

* * * * *